United States Patent
Mayama

(10) Patent No.: US 7,923,581 B2
(45) Date of Patent: Apr. 12, 2011

(54) PROCESS FOR PRODUCING BIARYLPHOSPHINE COMPOUND

(75) Inventor: Daisuke Mayama, Tokyo (JP)

(73) Assignee: Nippon Chemical Industrial Co., Ltd., Tokyo (JP)

( * ) Notice: Subject to any disclaimer, the term of this patent is extended or adjusted under 35 U.S.C. 154(b) by 340 days.

(21) Appl. No.: 12/230,083

(22) Filed: Aug. 22, 2008

(65) Prior Publication Data

US 2009/0054690 A1    Feb. 26, 2009

(30) Foreign Application Priority Data

Aug. 24, 2007    (JP) ................. 2007-218121

(51) Int. Cl.
C07F 9/50    (2006.01)
(52) U.S. Cl. .......................................... 568/8
(58) Field of Classification Search .................. None
See application file for complete search history.

(56) References Cited

U.S. PATENT DOCUMENTS

| | | | |
|---|---|---|---|
| 5,399,771 A | 3/1995 | Cai et al. | |
| 6,124,476 A | 9/2000 | Guram et al. | |
| 6,307,087 B1 | 10/2001 | Buchwald et al. | |
| 6,333,435 B1 | 12/2001 | Cai et al. | |
| 7,026,498 B2 | 4/2006 | Buchwald et al. | |
| 7,208,633 B2 * | 4/2007 | Goto et al. | 568/17 |
| 2005/0277772 A1 * | 12/2005 | Carreira | 544/225 |

FOREIGN PATENT DOCUMENTS

JP    2000-7688 A    1/2000
WO    WO 2005121157    * 12/2005

OTHER PUBLICATIONS

Ter Halle et al., {"Diam-BINAP"; a highly efficient monomer for the synthesis of heterogeneous enantioselective catalysts, Tetrahedron Letters (2000), 41(5), 643-646}.*
Lacey et al. {Synthesis and resolution of 2-methyl-Quinazolinap, a new atropisomeric phosphinamine ligand for asymmetric catalysis, Tetrahedron Letters (2000), 41(14), 2475-2478}.*
Knoepfel et al., {Catalytic, Enantioselective, Conjugate Alkyne Addition, Journal of the American Chemical Society (2005), 127(27), 9682-9683}.*
Ager et al., Chemical Communications, 1997, 2359-2360.
Vondenhof et al., Tetrahedron Letters, vol. 31, No. 7, pp. 985-988, 1990.

* cited by examiner

Primary Examiner — Kamal A Saeed
(74) Attorney, Agent, or Firm — Birch, Stewart, Kolasch & Birch, LLP

(57) ABSTRACT

A process for producing a biarylphosphine compound is disclosed. The process has a step of subjecting a biarylsulfonate compound to coupling reaction with a hydrogen-phosphine compound in the presence of a catalyst and an organic strong base to obtain a biarylphosphine compound. As the catalyst, preferably used is a nickel compound or a palladium compound. As the organic strong base, preferably used is 1,8-diazabicyclo[5.4.0]undecene-7 (DBU).

5 Claims, No Drawings

PROCESS FOR PRODUCING BIARYLPHOSPHINE COMPOUND

FIELD OF THE INVENTION

The present invention relates to a process for producing a biarylphosphine compound. A biarylphosphine compound obtained according to the present invention is used mainly as a ligand of a transition metal complex. The complex may be extensively used as a good catalyst for various organic reactions.

BACKGROUND OF THE INVENTION

A biarylphosphine compound is frequently used as a ligand of a transition metal complex. The complex is extensively used as a good catalyst for various organic reactions. As the organic reaction in which the transition metal complex is effective as a catalyst, there may be mentioned a cross-coupling reaction in which a halogenated aryl is reacted with an arylboronic acid or a primary/secondary amine to obtain a corresponding biaryl compound or arylamine compound, and a hydroformylation reaction in which an aldehyde is synthesized by the carbon homologation of alkenes with carbon monoxide.

A biarylphosphine compound is a useful compound in an extensive field including the ligand as mentioned above. However, in the existing synthetic methods, an expensive material is often used as a starting raw material and the synthesis is often accompanied by danger.

The process for producing a biarylphosphine compound, which has been reported up to now, may be classified into the following two techniques.

As the first production process, for example, as shown in the following reaction formula, there may be mentioned a technique in which a halogenated biaryl is metalized with magnesium or lithium, followed by coupling a halogenophosphine (U.S. Pat. No. 6,307,087 and U.S. Pat. No. 7,026,498).

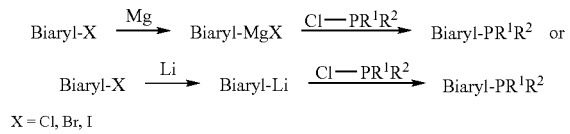

Although the production process is a useful technique because an intended product may be obtained in a reasonable yield the halogenated biaryl as a starting raw material is frequently difficult to obtain commercially. In addition, an absolute anhydrous condition is required for handling an organic metal and the handling is accompanied by danger because an organic metal itself is pyrophoric. Further, the production method has a limitation on the scope of the application, for example, it is not applicable to a substrate having a functional group reacting with an active organic metal, and the like.

As the second production process, there may be mentioned a technique in which a halogenated biaryl or biarylsulfonate is cross-coupled to a hydrogen-phosphine compound in the presence of a catalyst and a base. The production process may be shown, for example, by the following reaction formula (U.S. Pat. No. 6,124,476).

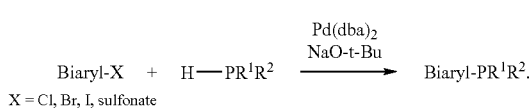

X in the reaction formula generally includes a halogen or a sulfonate (the example in U.S. Pat. No. 6,124,476 is a bromo group). If X is a sulfonate, since Biaryl-X may be easily obtained from an inexpensive phenol compound and a sulfonic acid anhydride or a halide, it is industrially advantageous in many cases. However, in practice, if there is used an inorganic base such as NaOt-Bu or KOt-Bu which is generally frequently used as a base as shown by the reaction formula, the sulfonate is hydrolyzed, thus significantly reducing the yield of the intended product in many cases.

As an improved process when a sulfonate is used as a raw material in the production process using the inorganic base, there is disclosed a production process in which an organic base is used in place of the inorganic base in order to prevent hydrolysis, for example, as shown by the following reaction formula (U.S. Pat. No. 5,399,771 and U.S. Pat. No. 6,333,435).

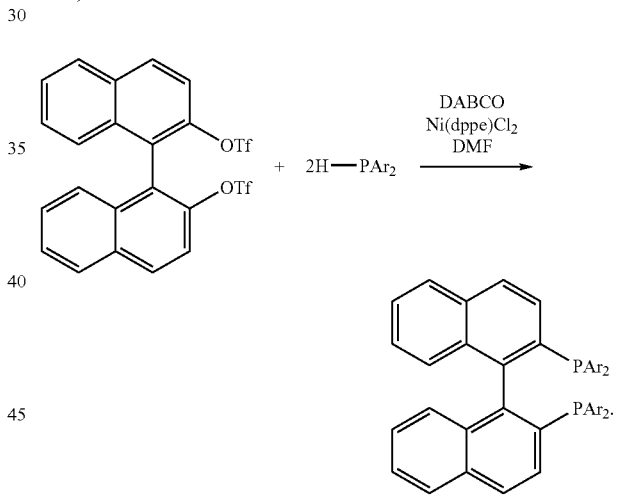

Ar = aryl

As the organic base used in the production process, there may be mentioned triethylamine, triisopropylamine, tributylamine, triethylenediamine (DABCO) and the like, and preferably used is DABCO. The production process is effective if a diarylphosphine is used as a hydrogen-phosphine compound as a starting raw material. However, the production process is not industrially applicable because the yield is low if a monoaryl monoalkyl phosphine or a dialkylphosphine is used as a hydrogen-phosphine compound.

In addition, in the second process, there is proposed a technique in which when a halogenated biaryl or biarylsulfonate is cross-coupled to a halogenophosphine by using the halogenophosphine in place of a hydrogen-phosphine compound, a reducing substance is used in addition to a catalyst and a base.

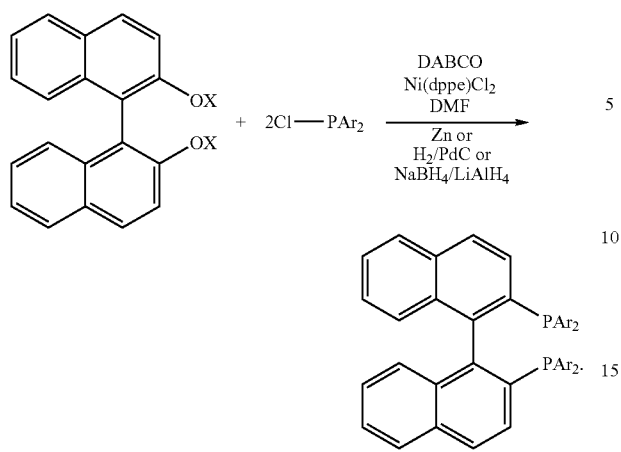

Ar = aryl, X = Cl, Br, I, OTf, etc.

In the production process, as the reducing substance, there may be used zinc powders (Chemical Communications 2359 (1997)), hydrogen (JP2000-7688A), sodium borohydride/lithium aluminum hydride (U.S. Pat. No. 7,208,633) and the like. The production process is effective if a halogenodiarylphosphine is used as a halogenophosphine, which is a starting raw material. However, as with the improved process using the organic base, the production process is not industrially applicable because of the yield is low if a monoaryl monoalkyl halogenophosphine or dialkylhalogenophosphine is used as a halogenophosphine.

Accordingly, in the present technical field, there has been desired a production process of obtaining biarylphosphine compounds by coupling a biarylsulfonate compound to an organic phosphine compound in an industrially advantageous manner.

SUMMARY OF THE INVENTION

The object of the present invention is to provide an industrially advantageous process for producing a biarylphosphine compound which is useful as a ligand of a transition metal complex used as a catalyst for an organic reaction.

The present invention is to provide a process for producing a biarylphosphine compound. The process has a step of subjecting a biarylsulfonate compound represented by general formula (1) to coupling reaction with a hydrogen-phosphine compound represented by general formula (2) in the presence of a catalyst and an organic strong base to obtain a biarylphosphine compound represented by general formula (3).

$$\text{Biaryl}\mathrm{-\!\!\!\!+\!E)}_n \quad (1)$$

wherein Biaryl represents a biaryl group, a substituted biaryl group, a biaryl heterocyclic group or a substituted biaryl heterocyclic group; E represents a sulfonate which is a leaving group, and n is an integer of 1 or more;

$$\text{H—PR}^1\text{R}^2 \quad (2)$$

wherein $R^1$ and $R^2$ represent a hydrogen atom, an alkyl group, a substituted alkyl group, a cycloalkyl group, a substituted cycloalkyl group, an aralkyl group, a substituted aralkyl group, an aliphatic heterocyclic group or a substituted aliphatic heterocyclic group, and $R^1$ and $R^2$ may be the same or different from each other or may be liked to each other to form a bond;

$$\begin{array}{c}(E)_l\\|\\\text{Biaryl}\mathrm{-\!\!\!\!+\!E)}_n\end{array} \quad (3)$$

wherein Biaryl, $R^1$, $R^2$ and E are the same as above; m is 1 or more, l is 0 or more, m and l each are an integer satisfying m+l=n, and n is the same as above.

DETAILED DESCRIPTION OF THE INVENTION

In general formulae (1) and (3), there will be explained a group represented by Biaryl (i.e., a biaryl group, a substituted biaryl group, a biaryl heterocyclic group, and a substituted biaryl heterocyclic group).

The biaryl group includes a biphenyl group, a binaphthyl group, a phenylnaphthyl group and the like. The specific structures are exemplified below.

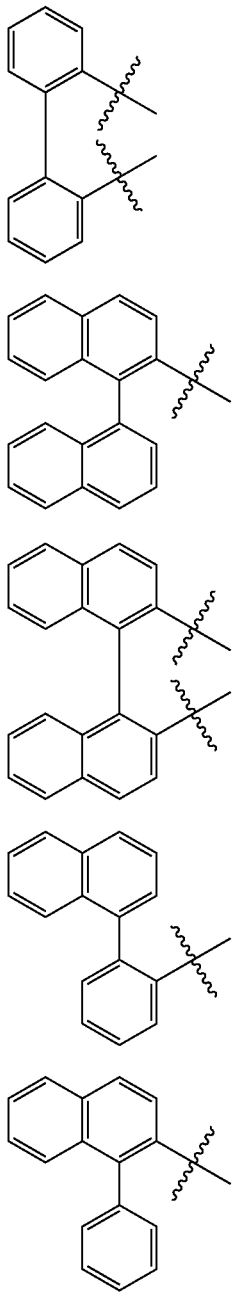

(a) biphenyl-2-yl group,
(b) biphenyl-3-yl-group,
(c) biphenyl-4-yl group,
(d) biphenyl-2,2′-diyl group,
(e) 1,1′-binaphthyl-2-yl group,
(f) 1,1′-binaphthyl-2,2′-diyl group,
(g) 2-(naphthyl-1-yl)phenyl group,
(h) 1-phenylnaphthyl-2-yl-group The substituted biaryl group includes a biaryl group in which at least one hydrogen atom of the biaryl group is substituted with a substituent such as an alkyl group, a cycloalkyl group, a halogenated alkyl group, an alkoxy group, a halogen atom, an amino group, an alkyl-substituted amino group and the like, and a biaryl group in which two adjacent hydrogen atoms of the biaryl group are substituted with a substituent such as an alkylenedioxy group and the like.

Among these substituents, a substituent which contains a carbon atom preferably has carbon atoms of 1 to 20. The specific structures of the substituted biaryl group are exemplified below.

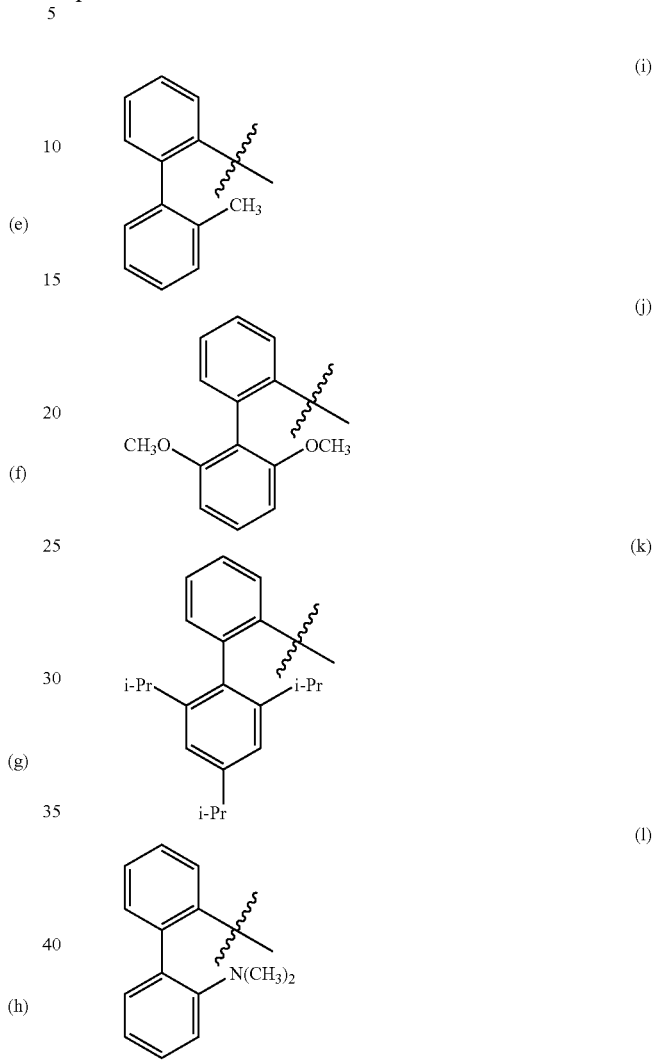

(i) 2′-methylbiphenyl-2-yl group,
(j) 2′,6′-dimethoxybiphenyl-2-yl group,
(k) 2′,4′,6′-triisopropylbiphenyl-2-yl group,
(l) 2′-dimethyl-aminobiphenyl-2-yl group The biaryl heterocyclic group is a biaryl heterocyclic group in which one or both of the two aryls composed of the biaryl group are substituted with an aromatic heterocyclic group. The aromatic heterocyclic group includes, for example, an aromatic heterocyclic group containing 1 to 3 hetero atoms such as a nitrogen atom, an oxygen atom, a sulfur atom and the like as a foreign atom. Among these, preferred are a five- or six-membered monocyclic aromatic heterocyclic group and a polycyclic aromatic heterocyclic group constituted by condensing plural five- or six-membered rings. The specific example includes a pyridyl group, an imidazolyl group, a thiazolyl group, a furfuryl group, a pyranyl group, a furyl group, a benzofuryl group, a thienyl group and the like.

The substituted biaryl heterocyclic group includes a biaryl heterocyclic group in which at least one hydrogen atom of the biaryl heterocyclic group is substituted with a substituent such as an alkyl group, a cycloalkyl group, a halogenated alkyl group, an alkoxy group, a halogen atom and the like.

Among these substituents, a substituent which contains a carbon atom preferably has the same number of carbon atoms as the substituted biaryl group.

In general formulae (1) and (3), the leaving group represented by E will be explained. The leaving group represented by E is a sulfonate, and the sulfonate includes methanesulfonate (mesylate), p-toluenesulfonate (tosylate), trifluoromethanesulfonate (triflate), benzenesulfonate, p-nitrobenzenesulfonate, perfluoroalkanesulfonate and the like. A preferred sulfonate is a triflate since it is commonly used and is eliminated successfully.

A biarylsulfonate compound represented by general formula (1) has n leaving groups (sulfonates) represented by E. n may be up to the number of the hydrogen atoms which directly bond to a biaryl skeleton in a biaryl compound inducing a group represented by Biaryl (that is, if the group represented by Biaryl is a substituted biaryl group or a substituted biaryl heterocyclic group, the hydrogen atoms in a substituent belonging to the biaryl compound which induces these groups are not included). For example, if the group represented by Biaryl is a biphenyl group, n is up to 10, and if it is 2'-methylbiphenyl-2-yl group, n is up to 9. However, given that the resulting biarylphosphine compound is used as a ligand of a transition metal complex and the like, the upper limit of n is preferably 2.

If n is 2 or more, the whole or part of plural Es (the number represented by m in general formula (3)) may be cross-coupled to be converted to a phosphino group ($-PR^1R^2$). The upper limit of m in general formula (3) is preferably 2, given that the resulting biarylphosphine compound is used as a ligand of a transition metal complex.

In general formulae (2) and (3), there will be explained a group which is represented by $R^1$ and $R^2$ (i.e., hydrogen atom, alkyl group, substituted alkyl group, cycloalkyl group, substituted cycloalkyl group, aralkyl group, substituted aralkyl group, aliphatic heterocyclic group, substituted aliphatic heterocyclic group).

The alkyl group may be linear or branched, and includes, for example, an alkyl group having carbon atoms of 1 to 6. Specifically, the alkyl group includes, a methyl group, an ethyl group, a n-propyl group, a 2-propyl group, a n-butyl group, a 2-butyl group, an isobutyl group, a tert-butyl group, a n-pentyl group, a 2-pentyl group, a tert-pentyl group, a 2-methylbutyl group, a 3-methylbutyl group, a 2,2-dimethylpropyl group, a n-hexyl group, a 2-hexyl group, a 3-hexyl group, a tert-hexyl group, a 2-methylpentyl group, a 3-methylpentyl group, 4-methylpentyl group, a 5-methylpentyl group and the like.

The substituted alkyl group includes an alkyl group in which at least one hydrogen atom of the alkyl group is substituted with a substituent such as an alkyl group, a cycloalkyl group, an alkoxy group, a halogen atom, an amino group or an amino group having a protective group or the like. Among these substituents, a substituent which contains a carbon atom preferably has carbon atoms of 1 to 20.

The cycloalkyl group includes, for example, a cycloalkyl group having carbon atoms of 3 to 16. Specifically, the cycloalkyl group includes a cyclopropyl group, a cyclobutyl group, a cyclopentyl group, a cyclohexyl group, a cycloheptyl group, a 2-methylcyclopentyl group, a 3-methylcyclopentyl group, a cycloheptyl group, a 2-methylcyclohexyl group, a 3-methylcyclohexyl group, a 4-methylcyclohexyl group, a menthyl group, a bornyl group, a norbornyl group, an adamantyl group and the like.

The substituted cycloalkyl group includes a cycloalkyl group in which at least one hydrogen atom of the cycloalkyl group is substituted with a substituent such as an alkyl group, a cycloalkyl group, an alkoxy group, a halogen atom, an amino group or an amino group having a protective group or the like. Among these substituents, a substituent having a carbon atom preferably has the same number of carbon atoms as the substituted alkyl group.

The aralkyl group includes, for example, an aralkyl group having carbon atoms of 7 to 12. Specifically, the aralkyl group includes a benzyl group, a 2-phenylethyl group, a 1-phenylpropyl group, a 2-phenylpropyl group, a 3-phenylpropyl group, a 1-phenylbutyl group, a 2-phenylbutyl group, a 3-phenylbutyl group, a 4-phenylbutyl group, a 1-phenylpentyl group, a 2-phenylpentyl group, a 3-phenylpentyl group, a 4-phenylpentyl group, a 5-phenylpentyl group, a 1-phenylhexyl group, a 2-phenylhexyl group, a 3-phenylhexyl group, a 4-phenylhexyl group, a 5-phenylhexyl group, a 6-phenylhexyl group and the like.

The substituted aralkyl group includes an arakyl group in which at least one hydrogen atom of the aralkyl group is substituted with a substitute such as an alkyl group, a cycloalkyl group, a halogenated alkyl group, an alkoxy group, a halogen atom, an amino group, an alkyl group-substituted amino group and the like. Among these substituents, a substituent having a carbon atom preferably has the same number of carbon atoms as the substituted alkyl group.

The aliphatic heterocyclic group includes, for example, an aliphatic heterocyclic group containing 1 to 3 hetero atoms such as a nitrogen atom, an oxygen atom, a sulfur atom and the like as a foreign atom, and preferred is a five- or six-membered aliphatic heterocyclic group. The specific example includes a pyrrolidyl-2-one group, a piperidino group, a piperadinyl group, a morpholino group, a tetrahydrofuryl group, tetrahydropyranyl group and the like.

The substituted aliphatic heterocyclic group includes an aliphatic heterocyclic group in which at least one hydrogen atom of the aliphatic heterocyclic group is substituted with a substitute such as an alkyl group, a cycloalkyl group, a halogenated alkyl group, an alkoxy group, a halogen atom and the like. Among these substituents, a substituent having a carbon atom preferably has the same number of carbon atoms as the substituted alkyl group.

In general formulae (2) and (3), $R^1$ and $R^2$ may be the same or different from each other and may be liked to each other to form a bond.

As the hydrogen-phosphine compound in which $R^1$ and $R^2$ in general formula (2) are bonded by linking, there may be specifically mentioned phosphabicyclo[3.3.1]undecane, phosphabicyclo[4.2.1]undecane, phosphorane, 2,5-dimethylphosphorane, 2,5-diethylphosphorane and the like.

There will be explained a coupling reaction of a biarylsulfonate compound represented by general formula (1) with a hydrogen-phosphine compound represented by general formula (2).

As for the loading ratio of the biarylsulfonate compound to the hydrogen-phosphine compound, the latter is in an amount of preferably 0.1 to 10 equivalents and more preferably 1 to 1.5 equivalents, based on the former. If there are plural Es in the biarylsulfonate compound, the whole or part of E may be converted into a phosphino group ($-PR^1R^2$) by adjusting the loading ratio accordingly.

As the preferred catalyst used in the coupling reaction, there may be mentioned a nickel compound and a palladium compound. The catalyst specifically includes nickel(0) carbonyl, nickel(II) chloride, nickel(II) bromide, nickel(II) acetate, bis(dibenzylidene acetone(dba)), palladium(0), palladium(II) chloride, palladium(II) acetate, tetrakis(triphenylphosphine)palladium(0), (2-methylallyl)palladium(II) chloride and the like. These may be a hydrate or a multimer.

The compounds exemplified as a catalyst may be used as they are, and the catalytic performance is improved more when they have a phosphine ligand than when they have no phosphine ligand.

The phosphine ligand includes, as a unidentate ligand, triphenylphosphine, triethylphosphine, tributylphosphine, tri-tert-butylphosphine, tricyclohexylphosphine, 2-(di-tert-butylphosphino)biphenyl (Johnphos), 2-(dicyclohexylphosphino)biphenyl (cyclohexyl Johnphos) and the like.

The phosphine ligand includes, as a bidentate ligand, bis(diphenylphosphino)methane (dppm), bis(diphenylphosphino)ethane (dppe), bis(diphenylphosphino)propane (dppf), bis(diphenylphosphino)butane (dppb), bis(diphenylphosphino)ferrocene (dppf), bis(di-tert-butylphosphino)ferrocene (d-t-Bu-pf), 2,2'-bis(diphenylphosphino)-1,1'-binaphthyl (BINAP), 2,2'-bis(dicyclohexylphosphino)biphenyl, 2-(dicyclohexylphosphino)-2'-(dimethylamino)biphenyl (Davephos), 4,5-bis(diphenylphosphino)-9,9-dimethylxanthene (Xanthphos), 9,9-dimethyl-4,5-bis(di-tert-butylphosphino)xanthene (t-Bu-Xanthphos) and the like.

As the catalyst, nickel(II) chloride is preferable because it is inexpensive. In addition, preferred is Ni(dppe)Cl$_2$ or palladium(II) acetate in order to increase the reactivity.

The amount of the catalyst to be added is preferably from 0.0001 to 100 mol %, more preferably from 0.01 to 10 mol %, based on the biarylphosphonate compound represented by general formula (1). In view of promoting the reaction properly while suppressing the amount of the catalyst to be added, the amount of the catalyst is most preferably from 0.1 to 5 mol %.

As the organic strong base used in the coupling reaction, there may be mentioned, for example, an organic strong base having the following structure.

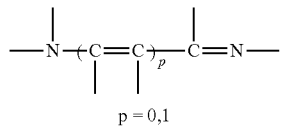

p = 0,1

As the organic strong base having the above structure, there may be specifically mentioned 1,8-diazabicyclo[5.4.0]undecene-7 (DBU), 1,5-diazabicyclo[4.3.0]nonene-5 (DBN), N,N-dimethylaminopyridine (DMAP) and the like, and among these, preferred is DBU.

The amount of the organic strong base to be added is preferably 0.5 to 10 equivalents, based on a biarylsulfonate compound represented by general formula (1). In view of promoting the reaction properly while suppressing the amount of the organic strong base to be added, the amount of the organic strong base is more preferably 1 to 2 equivalents.

The coupling reaction may be performed in a solvent. As the solvent used in the production process of the present invention, there may be mentioned a solvent which is frequently used in a general organic chemical reaction, that is, toluene, hexane, tetrahydrofuran (THF), dioxane, ethyl acetate, chlorobenzene and the like. The preferred solvent includes an amide compound having a strong basic property, which has the following structure.

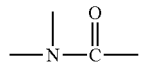

As the amide compound having the above structure, there may be specifically mentioned N,N-dimethylformamide (DMF), N,N-dimethylacetoamide (DMA), N-methylpyrrolidone (NMP), 1,3-dimethyl-2-imidazolidinone (DMI) and the like. Among these, preferred is DMF.

The amount of the solvent to be added is preferably 0.1 to 100 L/mol based on the biarylsulfonate compound represented by general formula (1). The amount of the solvent to be added is set accordingly in consideration of the fluidity of the reaction mixture at the time of the reaction and the effect of the solvent on the reaction.

The reaction temperature of the coupling reaction is preferably from 0 to 200° C., more preferably from 80 to 120° C. In view of promoting the reaction properly and suppressing the side reaction, the reaction temperature is most preferably from 100 to 110° C.

The reaction time of the coupling reaction is preferably from 1 minute to one week, more preferably from 3 to 48 hours. In view of the enough time to complete the reaction, the reaction time is most preferably from 6 to 24 hours.

The biarylphosphine compound synthesized by the production process of the present invention may be used as a reaction solution or may be used through a typical aftertreatment and a purification procedure such as solvent removal, separatory washing, crystallization, distillation, sublimation and column chromatography.

The biarylphosphine compound obtained by the production process of the present invention is useful as a ligand of a transition metal complex used as a catalyst for various organic reactions.

Since the production process of a biarylphosphine compound of the present invention proceeds with an excellent reaction catalytic activity, it is extremely useful industrially, and a desired biarylphosphine compound can be obtained in a shortened steps without serious danger.

When summing up the clear advantages of the production process of a biarylphosphine compound of the present invention compared to the conventional production process, they are as follows.

1) The present production process, which uses a hydrogen-phosphine compound as a starting material, is higher in reactivity than the conventional production process using a halogenophosphine compound. In addition, difficult-to-handle organic metals which require an absolute anhydrous condition are not required to be used and such organic metals are not required to be used as intermediate products. Further, unlike a halogenophosphine compound, a hydrogen-phosphine compound does not produce a halogenated hydroacid by hydrolysis, and thus it can be handled in a vessel which is not especially acid resistant.

2) Compared to the conventional production process using a biaryl halogenated product as a starting material, the present production process using a biarylsulfonate compound can use an inexpensive material of a biphenolic compound as the raw material, and therefore the variations of the resulting products are increased.

3) Compared to the conventional production process using a hydrogen-phosphine compound and a biaryl halogenated product or a biarylsulfonate compound as a starting material and an inorganic base such as NaO-t-Bu as a base, the present production process can produce an intended product with a high yield because there is substantially no possibility to disappear the starting material by hydrolysis even though the starting material is a sulfonate.

4) Compared to the conventional production process using a hydrogen-phosphine compound and a biarylsulfonate compound as a starting material and using triethylamine, triisopropylamine, tributylamine or DABCO as a base, the present production process can produce an intended product with a high yield even though not only an arylphosphine but an alkylphosphine is employed as a hydrogen-phosphine compound.

EXAMPLES

Hereinafter, the present invention will be specifically explained with reference to Examples and the like, but the scope of the present invention is not limited thereby. Unless otherwise specified, "%" indicates "% by weight".

All the synthetic operations were carried out by using sufficiently dried glass vessels. The reaction was carried out under a nitrogen atmosphere.

There was used a biarylsulfonate compound as a starting material which was synthesized by reacting the corresponding biaryl compound with sulfonic acid anhydride or a halide in the presence of a base. The procedure is shown in Tetrahedron Lett. 31 (1990) 985, which is incorporated herein by reference.

There was used an industrial product, hydrogen-phosphine compound as a starting material, produced by Nippon Chemical Industrial Co., Ltd.

There were used general reagents of metal compounds such as $Pd(OAc)_2$, $NiCl_2$ and the like, and organic strong bases as a catalyst.

There were used general reagents (not especially dehydrated) as a solvent.

The NMR spectrum measurement was performed by an NMR apparatus manufactured by JEOL ($^1H$; 300 MHz, $^{13}C$; 75.4 MHz, $^{31}P$; 121.4 MHz). Tetramethylsilane ($^1H$) and deuterated chloroform ($^{13}C$) were used as an internal standard, and 85% phosphoric acid ($^{31}P$) was used as an external standard.

The GC analysis was performed by GC-14B FID detector manufactured by Shimadzu Corporation.

The mass spectrometry was performed by GC-MS manufactured by Shimadzu Corporation.

Example 1

Production of 2-(dicyclohexylphosphino)biphenyl

A 50 cc glass vessel was equipped with a magnetic stirring bar, a pressure gauge, a syringe loading opening, a nitrogen valve and a vacuum valve. To the glass vessel were added 3.08 g (10.2 mmol) of biphenyl-2-yl-triflate, 3.12 g (20.5 mmol) of DBU, 262.7 mg (0.50 mmol) of Ni(dppe)$Cl_2$, 20 cc of DMF and 2.98 g (15.0 mmol) of dicyclohexylphosphine under a nitrogen atmosphere. The reaction mixture was stirred and aged overnight (18 hours and 40 minutes) in an oil bath at 100° C. under a nitrogen atmosphere.

The reaction solution was concentrated, and to the residue were added 20 cc of toluene and 10 g of 5% hydrochloric acid, followed by shaking and separating. The resulting organic layer was washed with 10 cc of water, 20 g of 2.5% sodium bicarbonate aqueous solution and 10 cc of water in this order. The organic layer was returned to a reaction flask, followed by concentrating to obtain a colored oil. The resulting colored oil was recrystallized and purified with 20 cc of methanol to obtain colorless powders (yield amount: 2.74 g (7.82 mmol)), yield: 77%). The resulting colorless powders were confirmed to be 2-(dicyclohexylphosphino)biphenyl, which was an intended product. The analytical results of the resulting colorless powders are shown below.

Quality: GC purity 98.0%
Characteristics: GC-MS: 349, 350 (FW350.48), mp: 103.4 to 104.6° C.
$^1H$-NMR (CDCl$_3$); 0.95-1.30 (10H, m), 1.50-1.75 (10H, m), 1.75-1.90 (2H, m), 7.25-7.44 (8H, m), 7.56-7.74 (1H, m)
$^{31}P$-NMR; −12.6

Example 2

Production of 2-(di-tert-butylphosphino)biphenyl

To a 100 cc glass vessel was equipped with a magnetic stirring bar, a nitrogen valve and a vacuum valve. Firstly, to the glass vessel were added 11.1 mg (0.049 mmol) of Pd(OAc)$_2$, 30.1 mg (0.101 mmol) of 2-(di-tert-butylphosphino)biphenyl (used a ligand) and 4 cc of DMF under a nitrogen atmosphere. The reaction mixture was stirred and aged at 80° C. or higher for 10 minutes. The reaction solution was cooled, followed by adding 3.04 g (10.1 mmol) of biphenyl-2-yl-triflate, 3.04 g (19.9 mmol) of DBU, 20 cc of DMF and 1.98 g (13.5 mmol) of di-tert-butylphosphine under a nitrogen atmosphere. The reaction solution was stirred and aged for one hour in an oil bath at 100° C., followed by further stirring and aging overnight (19 hours) at 110° C. under a nitrogen atmosphere. The resulting reaction solution was analyzed by GC to confirm the disappearance of biphenyl-2-yl-triflate.

The reaction solution was concentrated, and to the residue were added 20 cc of toluene and 20 cc of water, followed by shaking and separating. The resulting organic layer was washed with 10 cc of water twice, followed by drying with 5 g of anhydrous sodium sulfate. Thereafter, the following operations were carried out in order to remove palladium. That is, 15 g of a silica gel (Wako gel C200) was dissolved in toluene and then placed and dried on a glass filter, followed by passing through the organic layer. The resulting eluate was concentrated to obtain a brown oil. The brown oil was recrystallized and purified with 15 cc of methanol to obtain slightly colored powders (yield amount 2.04 g (6.84 mmol), yield 68%). The resulting slightly colored powders were confirmed to be 2-(dicyclohexylphosphino)biphenyl, which is an intended product. The analytical results of the resulting slightly colored powders are shown below.

Quality: GC purity 99.3%
Characteristics: GC-MS: 297, 299 (FW298.40), mp: 86.6 to 88.4° C.
$^1H$-NMR (CDCl$_3$); 1.13 (18H, d, 11.4 Hz), 7.2-7.45 (8H, m), 7.85-7.95 (1H, m)
$^{31}P$-NMR; 15.6 (m)

Examples 3 to 5 and Comparative Examples 1 to 3

A biphenyl-2-yl phosphine compounds were obtained in the same manner as Example 1 except for changing the type of a hydrogen-phosphine compound, catalyst, base and solvent used, as shown in Table 1.

In addition, in all the Examples and Comparative Examples, biphenyl-2-yl-triflate was used as a biarylsulfonate compound, and 1.5 equivalents of a hydrogen-phosphine compound and 2 equivalents of a base were used, based on biphenyl-2-yl-triflate. Further, the reaction time was set to 16 to 24 hours (overnight).

In Examples 1 to 5 and Comparative Examples 1 to 3, the compounds used and the results of the reaction yield and the like are shown in Table 1.

TABLE 1

| | Hydrogen-Phosphine Compound | Catalyst | Base | Solvent | Reaction Yield (%)[a] | Isolation Yield (%) |
|---|---|---|---|---|---|---|
| Example 1 | $HPCy_2$ | $Ni(dppe)Cl_2$ 5 mol %<br>$Pd(OAc)_2$ 0.5 mol % | DBU | DMF | >95 | 77 |
| Example 2 | $HP(t\text{-}Bu)_2$ | 2-(di-tert-butylphosphino)biphenyl 1 mol % | DBU | DMF | >95 | 68 |
| Example 3 | $HPCy_2$ | $NiCl_2 \cdot 6H_2O$ 5 mol % | DBU | DMF | 90 | — |
| Example 4[b] | $HP(t\text{-}Bu)_2$ | $Pd(OAc)_2$ 0.5 mol % | DBU | DMF | >95 | — |
| Example 5[b] | $HP(t\text{-}Bu)_2$ | $Pd(OAc)_2$ 0.5 mol % | DBU | Toluene | 90 | — |
| Comparative Example 1 | $HPCy_2$ | None | DBU | DMF | 0 | — |
| Comparative Example 2 | $HPCy_2$ | $Ni(dppe)Cl_2$ 5 mol % | DABCO | DMF | 8 | — |
| Comparative Example 3 | $HP(t\text{-}Bu)_2$ | $Ni(dppe)Cl_2$ 5 mol % | KOt-Bu | DMF | Hydrolysis | — |

[a]The reaction yield determined by GC, Area of Product/(Area of Triflate and Area of Product)
[b]The reaction temperature was set to 110° C.

What is claimed is:

1. A process for producing a biarylphosphine compound comprising a step of subjecting a biarylsulfonate compound represented by general formula (1) to coupling reaction with a hydrogen-phosphine compound represented by general formula (2) in the presence of a catalyst and an organic strong base to obtain a biarylphosphine compound represented by general formula (3),

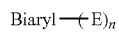  (1)

wherein Biaryl represents a biaryl group, a substituted biaryl group, a biaryl heterocyclic group or a substituted biaryl heterocyclic group; E represents a sulfonate which is a leaving group, and n is an integer of 1 or more;

H—$PR^1R^2$  (2)

wherein $R^1$ and $R^2$ represent a hydrogen atom, an alkyl group, a substituted alkyl group, a cycloalkyl group, a substituted cycloalkyl group, an aralkyl group, a substituted aralkyl group, an aliphatic heterocyclic group or a substituted aliphatic heterocyclic group, and $R^1$ and $R^2$ may be the same or different from each other or may be linked to each other to form a bond;

  (3)

wherein Biaryl, $R^1$, $R^2$ and E are the same as above; m is 1 or more, l is 0 or more, m and l each are an integer satisfying m+l=n, and n is the same as above;

and wherein the organic strong base has the following structure:

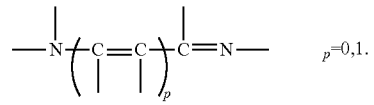

2. The process for producing a biarylphosphine compound according to claim 1, wherein the catalyst is a nickel compound or a palladium compound.

3. The process for producing a biarylphosphine compound according to claim 2, wherein the catalyst has a phosphine ligand.

4. The process for producing a biarylphosphine compound according to claim 1, wherein $R^1$ and $R^2$ independently represent an alkyl group, a substituted alkyl group, a cycloalkyl group or a substituted cycloalkyl group.

5. The process for producing a biarylphosphine compound according to claim 1, wherein the organic strong base is 1,8-diazabicyclo[5.4.0]undecene-7,1,5-diazabicyclo[4.3.0]nonene-5 or N,N-dimethylaminopyridine.

* * * * *